(12) United States Patent
Guillou et al.

(10) Patent No.: US 7,186,674 B2
(45) Date of Patent: Mar. 6, 2007

(54) TOPICAL CLEANSING COMPOSITION

(75) Inventors: Veronique Guillou, Antony (FR); Laurence Sebillotte-Arnaud, L'Hay les Roses (FR); Dominique Bordeaux, Longpont sur Orge (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/901,907

(22) Filed: Jul. 11, 2001

(65) Prior Publication Data
US 2002/0037267 A1    Mar. 28, 2002

(30) Foreign Application Priority Data
Jul. 12, 2000 (FR) .................................. 00 09111

(51) Int. Cl.
B01F 17/14 (2006.01)
C11D 9/00 (2006.01)
(52) U.S. Cl. ..................... 510/130; 424/401; 424/70.1; 424/70.23; 510/119
(58) Field of Classification Search ............... 510/119, 510/130, 475, 120, 123, 124, 125; 514/944; 424/70.1, 70.11, 70.15, 70.19, 70.22, 70.23, 424/70.31, 401
See application file for complete search history.

(56) References Cited

U.S. PATENT DOCUMENTS

| 4,139,485 | A | * | 2/1979 | Imokawa et al. ........... 252/135 |
| 4,381,259 | A | | 4/1983 | Homma et al. |
| 5,326,483 | A | * | 7/1994 | Halloran et al. ........ 252/175.15 |
| 5,653,970 | A | | 8/1997 | Vermeer |
| 6,090,773 | A | * | 7/2000 | Lukenbach et al. .......... 510/475 |
| 6,200,937 | B1 | * | 3/2001 | Brenman et al. ........... 510/119 |
| 6,258,771 | B1 | * | 7/2001 | Hsu et al. .................... 510/418 |
| 6,262,130 | B1 | * | 7/2001 | Derian et al. .................. 516/56 |
| 6,391,834 | B1 | * | 5/2002 | Schelges et al. .............. 510/23 |

FOREIGN PATENT DOCUMENTS

| DE | 199 37 917 | 2/2001 |
| WO | WO 94/17783 | 8/1994 |

OTHER PUBLICATIONS

Mottram, "Hair Shampoos", 1993, Poucher's Perfumes, Cosmetics and Soaps, vol. 3, Chapman & Hall Inc., (9$^{th}$ ed. Hilda Butler), pp. 176-191.*
Derwent Abstracts, AN 1988-231723, JP 63-165477, Jul. 8, 1988.

* cited by examiner

Primary Examiner—Sreeni Padmanabhan
Assistant Examiner—Gina C. Yu
(74) Attorney, Agent, or Firm—Oblon, Spivak, McClelland, Maier & Neustadt, P.C.

(57) ABSTRACT

A cleansing composition, which comprises at least one phosphate surfactant, at least one foaming nonionic surfactant and at least one cationic polymer devoid of saccharide groups in an aqueous medium, the composition having the appearance of a transparent gel.

16 Claims, 1 Drawing Sheet

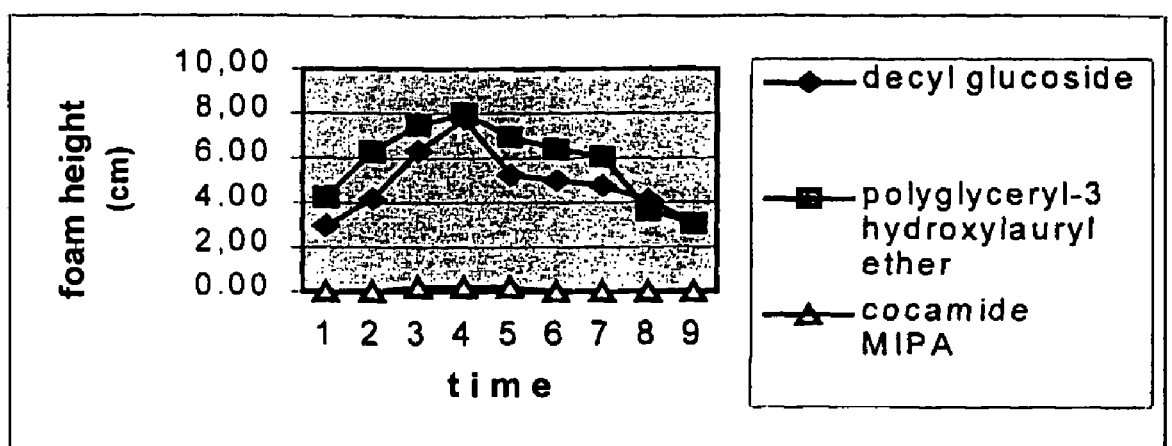

TOPICAL CLEANSING COMPOSITION

BACKGROUND OF THE INVENTION

1. Field of the Invention

The present invention relates to a foaming cleansing composition, which can be removed by rinsing the skin with water and which has the appearance of a transparent gel, and which comprises a surfactant of the phosphate type, a foaming nonionic surfactant and a cationic polymer and to its uses in the cosmetic or dermatological fields. More particularly, the invention relates to a product for cleansing or removing make-up from the skin, the scalp and/or the hair.

2. Description of the Background

Cleansing the skin is very important for the care of the face. The cleansing process must be as efficient as possible because greasy residues, such as excess sebum, the remnants of cosmetic products used daily, and make-up products, in particular waterproof products, accumulate in the skin folds and can block the pores of the skin and result in the appearance of spots.

The use of foaming detergent aqueous gels for cleansing the skin is known. Their cleansing action is attributable to the surfactants which they comprise, these surfactants suspending the greasy residues and the pigments of the make-up products. These gels are effective and pleasant to use because they foam. There is a search in particular to prepare transparent foaming cleansing gels because, just like water, transparency is the symbol of purity and thus of cleanliness and transparent gels are thus particularly appreciated by users. The transparent foaming gels intended for cleansing the face or the body very often generate light airy foams. However, after rinsing, the skin is often slippery and the sensation of a clean skin is no longer experienced because of the presence of a film-forming residue on the skin which is difficult to remove. One way of obtaining dense foams with fine bubbles, which are quickly rinsed off without leaving a film, consists in using soaps (fatty acid salts) as the main surfactants. However, soap compositions are less well tolerated, particularly by sensitive skin. In addition, they are not transparent. A need therefore continues to exist for a foaming aqueous gel which does not comprise soap and which has a good foam quality while having a good rinsing quality and good eye and skin tolerance.

SUMMARY OF THE INVENTION

Accordingly, one object of the present invention is to provide a cleansing composition in the form of a foaming transparent gel which has both good cosmetic properties (qualities of foam and quality of rinsing) and good tolerance properties.

Briefly, this object and other objects of the present invention as hereinafter will become more readily apparent can be attained in a composition which is a combination of a surfactant of the phosphate type, a foaming nonionic surfactant having specific foaming properties and a cationic polymer devoid of saccharide groups.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawings, wherein:

The FIGURE shows the foam heights of several nonionic surfactants which are decyl glucoside, polyglyceryl-3-hydroxylauryl ether and cocamide MIPA versus time.

DETAILED DESCRIPTION OF THE PREFERRED EMBODIMENTS

The preparation of foaming compositions comprising phosphate type surfactants is certainly known. Thus, GB 2,283,755 discloses a combination of MAP (monoalkyl phosphate), which is a non-phosphate surfactant, and a skin conditioning polymer in the preparation of foaming cleansing products. Foaming nonionic surfactants are not described among the non-phosphate surfactants and the compositions described in this document exhibit the disadvantage of giving a foam which has neither sufficient density nor sufficient volume.

Another publication, EP 3 337 354, discloses the combination of alkylpolyglucosides (APG) and cationic polymers. However, the compositions disclosed in this publication exhibit the disadvantage of generating a rough foam and of leaving a film on the skin after rinsing.

Accordingly, the cleansing composition of the present application which has the appearance of a transparent gel and which comprises, in a physiologically acceptable aqueous medium, at least one surfactant of the phosphate type, at least one foaming nonionic surfactant and at least one cationic polymer devoid of saccharide groups, is distinctly different from these known compositions.

The term "physiologically acceptable medium" in the present invention is understood to mean a medium that is compatible with the skin, mucous membranes, scalp, eyes and/or hair. Furthermore, it is an aqueous medium, that is to say, a medium comprising an amount of water which is at least 35% by weight, preferably ranging from 35% to 95% by weight and better still from 40% to 80% by weight, with respect to the total weight of the composition.

The word "transparent" means that the composition has, a turbidity of less than or equal to 500 NTU. NTUs (Nephelometric Turbidity Units) are the units of measurement of the turbidity of a composition. The turbidity measurement can be made, for example, with a model 2100P turbidimeter from Hach Compagny, the tubes used for the measurement being referenced as AR397A cat 24347-06. The measurements are made at ambient temperature of about 20° C. to 25° C. The transparency of a composition can be measured either by the coefficient of transmission at 600 nm or by the turbidity. The composition of the invention has a coefficient of transmission at 600 nm ranging from 10% to 90% or else a turbidity ranging from 2 to 500 NTU and preferably from 5 to 300 NTU.

The viscosity of the compositions of the invention preferably ranges from 0.1 to 200 poises (0.01 to 20 Pa-s) and better still from 5 to 100 poises (0.5 to 10 Pa-s), measured at 25° using the Rheomat RM180 from Rheometric Scientific, this device being equipped with a different rotor depending on the viscosities, for example, with a rotor 2 for viscosity ranges of less than 7 poises, with a rotor 3 for viscosity ranges of 2 to 40 poises and with a rotor 4 for viscosity ranges of 20 poises to 80 poises.

The combination of the surfactant of the phosphate type and the foaming nonionic surfactant with the cationic polymer not comprising a saccharide group makes it possible to obtain a voluminous foam with small bubbles which is soft and dense. On the contrary, if the cationic polymer not comprising a saccharide group is replaced by a cationic polysaccharide derivative, such as a cationic derivative of guar gum, of cellulose, of starch or of galactomannan, the composition obtained leaves a slippery film on the skin, upon rinsing which is not very pleasing to users. In addition, the cationic derivatives of guar gum have a tendency to leave a sticky film.

The compositions of the invention have the advantage of being very stable and of exhibiting neither phase separation nor the phenomena of recrystallization on storage at a temperature ranging from 4° C. to 45° C., even if they are subjected to −20° C./+20° C. cycle Surfactant of the Phosphate Type The surfactant of the phosphate type is selected from monoalkyl phosphates, dialkyl phosphates, their salts and their mixtures. These monoalkyl phosphates and dialkyl phosphates comprise one or more linear or branched and aliphatic and/or aromatic alkyl chains having from 8 to 22 carbon atoms. In the mixture of mono- and dialkyl phosphates, the mono/di ratio can range from 100/0 to 50/50. These phosphates can be neutralized with organic or inorganic bases, such as potassium hydroxide, sodium hydroxide, triethanolamine, arginine, lysine and N-methylglucamine.

Suitable examples of the phosphate type surfactants of the composition of the invention include monolauryl phosphate, such as the product sold under the name MAP 20® by Kao Chemicals, the potassium salt of dodecyl phosphate, such as the mixture of mono- and diester (predominantly diester) sold under the name Crafol AP-31© by Cognis, the octyl monoester and the octyl diester of phosphoric acid, such as the mixture sold under the name Crafol AP-20® by Cognis, the ethoxylated (7 mol. of EO) 2-butyloctanol monoester and the ethoxylated (7 mol. of EO) 2-butyloctanol diester of phosphoric acid, such as the mixture sold under the name Isofol 12 7 EO-Phosphate Ester® by Condea, the potassium or triethanolamine salts of monoalkyl ($C_{12}$–$C_{13}$) phosphate, such as the product sold under the references Arlatone MAP 230K-40® and Arlatone MAP 230T-60® by Uniqema, potassium lauryl phosphate, such as the product as a 40% aqueous solution sold under the name Dermalcare MAP XC99/09© by Rhodia Chimie, and the mixtures of these surfactants.

The amount of surfactant(s) of the phosphate type can range, for example, from 1% to 50% by weight of active material and preferably from 1.5% to 20% by weight of active material with respect to the total weight of the composition.

Nonionic Surfactant

The nonionic surfactants used in the composition of the invention are foaming surfactants, that is to say that they generate a foam height H as described below which is equal to or greater than 3 cm and preferably equal to or greater than 5 cm.

Determination of the Foam Height of a Surfactant

The foam height produced by a surfactant is determined by characterization of the foaming behavior under vortex agitation. The following are observed:

the kinetics of the rise of the foam, the ability to refoam after the addition of water the stability over time of the foam formed.

The equipment used is a Heidolph REAR 2000 vortex-type vibratory agitator equipped with round-bottomed glass tubes (height 15 cm, diameter 2 cm) having screw stoppers, a holder for storing these tubes, an indelible felt-tipped pen and a ruler.

An aqueous surfactant solution, comprising 13% of active material, is prepared in deionized water, and adjusted to pH 7 with a citric acid or potassium hydroxide solution.

The test is conducted in the following manner:

The Vortex is switched on in the continuous position and at the maximum speed 9.

The tube filled with the solution is positioned on the Vortex and is supported vertically by the index finger, between the thumb and the middle finger, for 15 seconds. After halting the agitation, two lines are drawn on the tube with the felt-tipped pen, corresponding to the foam height=height at time 1.

The tube is inverted once, making sure that the liquid and the foam are mixed, then it is again positioned on the Vortex and the same step as previously is followed; agitation is allowed to take place for 30 seconds and the level is recorded, which level=height at time 2.

The tube is inverted once, is then again positioned on the Vortex and the same step as previously is followed; agitation is allowed to take place for 1 minute and the level is recorded, which level=height at time 3.

After this final measurement, 7.0 g of deionized water is added to the tube.

The tube is inverted 3 times and is reagitated for 30 seconds on the Vortex, the same step being followed, and the level is recorded, which level=height at time 4=height H.

The tube is placed on the holder and the levels are recorded after standing for 5 min, 10 min, 20 min, 30 min and 1 h=heights at times 5 to 9.

The foam height indicated by the lines on the tube is measured in centimeters.

The results are expressed in the form of graphs of foam heights as a function of time.

The FIGURE presents the foam heights for various nonionic surfactants. Cocamide MIPA exhibits foam heights from 1 to 9 of virtually zero, whereas decylglucoside and polyglyceryl-3 hydroxylauryl ether have foam heights which are approximately 3 or 4 cm at the start and have a height H (height at time 4) of approximately 8 cm, which is much greater than 5 cm. The nonionic surfactants used according to the invention have a foam height H preferably of greater than 3 cm and in particular equal to or greater than 5 cm.

Suitable examples of nonionic surfactants which may be used in the composition of the invention, include polyglycerolated fatty alcohols; esters of fatty acids and of polyol; alkoxylated alkamides; glucamine derivatives; alkylpolyglucosides; and their mixtures.

The polyglycerolated fatty alcohols are polyglyceryl alkyl ethers with an alkyl group comprising from 8 to 30 atoms and preferably from 10 to 20 carbon atoms. Suitable such fatty alcohols include polyglycerolated fatty alcohols, such as polyglycerolated (3.5 mol. of glycerol) dodecanediol or polyglyceryl-3 hydroxylauryl ether (INCI name), sold under the name Chimexane NF by Chimex.

The esters of fatty acids and polyols have a fatty chain comprising from 8 to 30 carbon atoms and preferably from 10 to 22 carbon atoms. The polyol can in particular be glycerol or glycerol polymers (polyglycerol) comprising several glycerol units. Suitable examples of such include esters of fatty acids and polyols, such as polyglycerol monolaurate, which is sold under the name Sunsoft M-12J by Taiyo Kagaku.

Another surfactant type is alkoxylated alkamides, such as ethoxylated alkamides of which PEG-5 cocamide (CTFA name) is an example and in particular the product sold under the name Genagen CA-050 by Clariant.

Still another surfactant type is N-alkylglucamine derivatives such as 2-ethylhexyloxycarbonyl-N-methylglucamine.

Particularly useful are alkylpolyglucosides, and those which possess an alkyl group comprising from 6 to 30 carbon atoms and preferably from 8 to 16 carbon atoms and which possess a hydrophilic (glucoside) group preferably comprising 1.2 to 3 saccharide units. Suitable alkylpolyglucosides include decylglucoside ((C9/C11)alkylpolyglucoside (1.4)), such as the product sold under the name Mydol 10 by Kao Chemicals, the product sold under the name Plantaren 2000 UP by Henkel and the product sold under the name Oramix NS 10 by Seppic; caprylyl/caprylglucoside, such as the product sold under the name Oramix CG 110 by Seppic; laurylglucoside, such as the products sold under the names Plantaren 1200 N and Plantacare 1200 by Henkel; and cocoglucosides, such as the product sold under the name Plantacare 818/UP by Henkel.

The amount of foaming nonionic surfactant(s) in the composition of the invention can range, for example, from 1 to 50% by weight of active material, preferably from 1.5% to 20% by weight of active material, with respect to the total weight of the composition.

Cationic Polymer Devoid of Saccharide Groups

The preferred cationic polymers are selected from those which possess units comprising primary, secondary, tertiary and/or quaternary amine groups which can either form part of the main polymer chain or be carried by a pendant substituent connected directly to the main polymer chain.

The cationic polymers used generally have a number-average molecular weight ranging from 500 to $5 \times 10^6$ approximately and preferably from $10^3$ to $3 \times 10^6$ approximately.

Suitable examples of cationic polymers of the invention include the following polymers and their blends:

(1) Homopolymers or copolymers of acrylic or methacrylic esters or amides comprising an anion derived from an inorganic or organic acid, such as a methyl sulfate anion or a halide, such as chloride or bromide. Suitable specific examples include:

copolymers of acrylamide and methacrylyloxyethyltrimethylammonium salt, such as the copolymer of acrylamide and β-methacrylyloxyethyltrimethylammonium chloride (INCI name: polyquaternium-15), for example the product sold under the name Rohagit KF 720 F by Rohm, and such as the copolymer of acrylamide and of β-methacrylyloxyethyltrimethylammonium methyl sulfate (INCI name: polyquaternium-5), for example the product sold under the name Merquat 5 by Calgon;

quaternized or nonquaternized vinylpyrrolidone/dialkylaminoalkyl acrylate or methacrylate copolymers, such as the quaternary ammonium polymer formed by reaction of diethyl sulfate and of a copolymer of vinylpyrrolidone and dimethylaminoethyl methacrylate (INCI name: polyquaternium-11), for example the products sold under the names Gafquat 755, Gafquat 755N and Gafquat 734 by ISP;

acrylic acid/methyl acrylate/methacrylamidopropyltrimonium chloride copolymers (INCI name: polyquaternium-47), such as the product sold under the name Merquat 2001N by Calgon.

(2) Alkyldiallylamine or dialkyldiallylammonium polymers, in particular homopolymers of dimethyldiallylammonium salt and copolymers of dimethydiallylammonium salt and acrylamide or of acrylic or methacrylic acid. Suitable such polymers include homopolymers of dimethyldiallylammonium chloride (INCI name: polyquaternium-6), such as the product sold under the name Salcare SC 30 by CIBA and the product sold under the name Merquat 100 by Calgon; the copolymer of dimethyldiallylammonium chloride and acrylamide (INCI name: polyquaternium-7), such as the products sold under the names Merquat S, Merquat 2200 and Merquat 550 by Calgon and the product sold under the name Salcare SC 10 by Ciba; the copolymer of dimethyldiallylammonium chloride and acrylic acid (INCI name: polyquaternium-22), such as the product sold under the name Merquat 280 by Calgon; or the polymeric ammonium salt of acrylic acid, or diallyldimethylammonium chloride and acrylamide (INCI name: polyquaternium-39), such as the product sold under the name Merquat Plus 3330 or 3331 by Calgon.

(3) Quaternary polymers of vinylpyrrolidone and imidazole or of vinylimidazole or methylvinylimidazole, such as the polymeric quaternary ammonium salt formed of methylvinylimidazolium chloride and vinylpyrrolidone (INCI name: polyquaternium-16), such as the products sold under the names Luviquat FC905, Luviquat FC370, Luviquat HMS52 and Luviquat FC550 by BASF; the polymeric quaternary ammonium salt formed of vinylpyrrolidone and quaternized imidazoline (INCI name: polyquaternium-44), such as the products sold under the names Luviquat Care and Luviquat MS-370 by BASF; or the polymeric quaternary ammonium salt formed by reaction of vinylcaprolactam and vinylpyrrolidone with methylvinylimidazolium methyl sulfate (INCI name: polyquaternium-46), such as the product sold under the name Luviquat sold by BASF.

(4) Vinylpyrrolidone polymers comprising methacrylamidopropyldimethylamine or methacrylamidopropyltrimethylammonium (M.A.P.T.A.C.) units (INCI name: polyquaternium-28), among which mention may in particular be made of the products sold under the names Gafquat HS-100 and Styleze CC-10 by I.S.P.

It is preferable, among the cationic polymers which may be used in the context of the present invention, to employ copolymers of acrylamide and methacrylyloxyethyltrimethylammonium salt, in particular polyquaternium-5; the acrylic acid/methyl acrylate/methacrylamidopropyltrimonium chloride copolymer (polyquaternium-47); copolymers of dimethyldiallylammonium chloride, in particular polyquaternium-7 and polyquaternium-39; the vinylpyrrolidone polymer comprising methacrylamidopropyldimethylamine or methacrylamidopropyltrimethylammonium units (polyquaternium-28); quaternary polymers of vinylpyrrolidone and imidazole, in particular polyquaternium-44; and the blends of these polymers.

These cationic polymers, in combination with the surfactant of phosphate type and the foaming nonionic surfactant, contribute softness to the foam, reduce the size of the bubbles, generally, and provide the desired rinsing characteristics.

The amount of cationic polymer(s) can range, for example, from 0.01% to 5% by weight of active material and preferably from 0.05% to 2% by weight of active material with respect to the total weight of the composition.

According to a preferred embodiment of the invention, the composition comprises (1) at least one surfactant of the phosphate type selected from monolauryl phosphate, the potassium salt of dodecylphosphate, the octyl monoester and octyl diester of phosphoric acid, the ethoxylated (7 mol. of EO) 2-butyloctanol monoester and the ethoxylated (7 mol. of EO) 2-butyloctanol diester of phosphoric acid, the potassium or triethanolamine salts of monoalkyl ($C_{12}$–$C_{13}$) phosphate, or potassium lauryl phosphate, (2) at least one foaming nonionic surfactant selected from alkylpolyglucosides and polyglycerolated fatty alcohols, and (3) at least one cationic polymer selected from polyquaternium-5, polyquaternium-47, polyquaternium-7, polyquaternium-39, polyquaternium-28 and polyquaternium-44.

According to a specific embodiment of the invention, the composition of the invention comprises potassium lauryl phosphate, decylglucoside and/or polyglyceryl-3 hydroxylauryl ether, and polyquaternium-7.

The aqueous medium of the foaming compositions of the invention can comprise, in addition to water, one or more solvents selected from lower alcohols comprising from 1 to 6 carbon atoms, such as ethanol; polyols, such as glycerol; glycols, such as butylene glycol, isoprene glycol, propylene glycol or polyethylene glycols, for example PEG-8; sorbitol; sugars, such as glucose, fructose, maltose, lactose or sucrose; and their mixtures. The amount of solvent(s) in the composition of the invention can range from 0.5% to 30% by weight and preferably from 5% to 20% by weight with respect to the total weight of the composition.

In order to obtain compositions which are fluid to a greater or lesser extent, it is possible to incorporate, in the compositions of the invention, one or more thickening agents, in particular polymers, in concentrations ranging, for example, from 0.05% to 10% by weight of active material, preferably from 0.2% to 5% by weight and better still from 0.02% to 2% by weight, with respect to the total weight of the composition.

Suitable examples of thickeners include inorganic salts, such as sodium chloride; or oxyethylenated molecules and in particular ethoxylated alkyl or acyl derivatives of polyols which can in particular be oxyethylenated derivatives of esters of fatty acids or of ethers of fatty alcohols and polyols, such as glycerol, sorbitol, glucose or pentaerythritol. Mention may be made, as compounds of this type, of, for example, oxyethylenated (200 EO) glyceryl stearate, such as the product sold under the name Simulsol 220 TM© by Seppic; oxyethylenated (150 EO) pentaerythrityl tetrastearate, for example the product sold under the name Crothix© by Croda, oxyethylenated (120 EO) methylglucose dioleate, for example the product sold under the name Glucamate DOE-120 Végétal © by Amerchol, or oxyethylenated (160 EO) sorbitan triisostearate, for example the product sold under the name Rheodol TW IS399C by Kao Chemicals.

In addition, the compositions of the invention can comprise adjuvants commonly used in the cosmetic field selected from fragrances, preservatives, sequestering agents (EDTA), pigments, pearlescent agents, inorganic or organic fillers, agents for adjusting the pH, soluble dyes, sunscreen agents or active principles. The amounts of these various adjuvants are those conventionally used in the field under consideration, for example, from 0.01% to 20% of the total weight of the composition. These adjuvants and their concentrations must be such that they do not modify the property desired for the composition of the invention.

The compositions of the invention have the appearance of a transparent gel. In addition, these compositions are stable and have very good rinsability. They can be used in particular in the cosmetic or dermatological fields and can constitute, for example, a product for cleansing and/or removing make-up from the skin, scalp and/or hair or a scrub and/or exfoliant for the skin. They can constitute more particularly a composition for cleansing the skin.

Another aspect of the invention is the cosmetic use of the composition as defined above as products for cleansing and/or removing make-up from the skin, scalp and/or hair and/or as a scrub and/or exfoliant for the skin.

The compositions of the invention can be used in two ways:

The first use consists in spreading the gel in the hands, in applying it to the face or to the body and in then massaging it in the presence of water to develop the foam directly on the face or the body.

The other possible use of this type of product consists in developing the foam in the palms of the hands before applying it to the face or the body. In both cases, the foam is subsequently removed by rinsing.

Another aspect of the invention is a cosmetic process for cleansing the skin, scalp and/or hair in which the composition of the invention is applied to the skin, to the scalp and/or to the hair in the presence of water. The foam which forms and the grime which is loosened are removed by rinsing with water.

The compositions of the invention can also constitute a composition for the treatment of greasy skin, in particular when they comprise a specific active principle for the treatment of greasy skin, such as, for example, salicylic acid, azelaic acid, triclosan, piroctone olamine or niacinamide (vitamin PP).

Still another aspect of the invention is the use of the composition as defined above in the preparation of a composition intended for the treatment of greasy skin.

Having now generally described this invention, a further understanding can be obtained by reference to certain specific examples which are provided herein for purposes of illustration only and are not intended to be limiting unless otherwise specified. The amounts shown are as % by weight, unless otherwise mentioned.

In the table below, all the percentages are expressed as weight of starting materials as sold commercially (and not as weight of active material A.M.).

| Composition | Comparative Ex. 1 | Comparative Ex. 2 | Comparative Ex. 3 | Ex. 1 according to the invention | Ex. 2 according to the invention | Ex. 3 according to the invention | Comparative Ex. 4 |
|---|---|---|---|---|---|---|---|
| Lauryl phosphate (1) | 13% | — | 6.5% | 6.5% | 3.35% | 6.5% | 6.5% |
| Decylglucoside (2) | — | 32.5% (A.M. = 13%) | 16.25% (A.M. = 6.5%) | 16.25% (A.M. = 6.5%) | 26.25% (A.M. = 10.5%) | — | — |
| Polyglyceryl-3 hydroxylauryl ether | — | — | — | — | — | 6.5% | — |
| Cocamide MIPA | — | — | — | — | — | — | 6.5% |

-continued

| Composition | Comparative Ex. 1 | Comparative Ex. 2 | Comparative Ex. 3 | Ex. 1 according to the invention | Ex. 2 according to the invention | Ex. 3 according to the invention | Comparative Ex. 4 |
|---|---|---|---|---|---|---|---|
| Polyquaternium-7 (3) | — | — | — | 5.7% | 5.7% | 2.3% | 2.3% |
| PEG-150 pentaerythrityl tetrastearate | — | — | — | 0.5% | 0.5% | — | 0.5% |
| Oxyethylated (200 EO) glyceryl monostearate (5) | — | — | — | — | — | 0.5% | — |
| Glycerol | 3.5% | 3.5% | 3.5% | 3.5% | 3.5% | 3.5% | 3.5% |
| Sorbitol | 3.5% | 3.5% | 3.5% | 3.5% | 3.5% | 3.5% | 3.5% |
| Potassium hydroxide | 3% | — | 1.7% | 1.7% | 0.9% | 1.7% | 1.7% |
| Hydroxypropyl-cellulose | — | — | — | 0.2% | 0.2% | 0.2% | 0.2% |
| Disodium EDTA | 0.05% | 0.05% | 0.05% | 0.05% | 0.05% | 0.05% | 0.05% |
| Sodium chloride | 0.1% | 0.1% | 0.1% | 0.1% | 0.1% | 0.1% | 0.1% |
| Preservatives | 0.3% | 0.3% | 0.3% | 0.3% | 0.3% | 0.3% | 0.3% |
| Water | q.s. for 100% | q.s. for 100% | q.s. for 100% | q.s. for 100% | q.s. for 100% | q.s. for 100% | q.s. for 100% |
| Appearance | solution | solution | solution | transparent gel | transparent gel | transparent gel | unstable opaque gel |

(1) Monolauryl phosphate (comprising 75% of monoester): MAP 20 ® from Kao Chemicals;
(2) (C9/11)Alkylpolyglucoside (1.4), as a 40% solution: Mydol 10 ® from Kao Chemicals;
(3) Dimethyldiallylammonium chloride/acrylamide copolymer at 8% in water: Merquat S ® from Calgon;
(4) Polyglycerolated (3.5 mol.) dodecanediol: Chimexane NF ® from Chimex;
(5) Oxyethylenated (150 EO) pentaerythrityl tetrastearate: Crothix ® from Croda.

Sensory performance: The foam qualities developed are evaluated according to the protocol described below.

Before any use of the product, the hands are washed with household soap and then suitably rinsed and dried. The protocol then followed is as follows:

1- the hands are rendered wet by passing them under running water and are shaken three times to roughly dry them, 2- 1 g of product is placed in the hollow of one of the hands, 3- the product is worked between both palms for 10 seconds, 4- 2 ml of water are added and the product is again worked for 10 seconds, 5- the hands are rinsed under water, 6- they are wiped dry.

The criteria are evaluated at each stage of the protocol followed and they are graded on a scale from 0 to 10.

Stage 4: evaluation of the foam quality

The foam volume: the grade attributed increases as the volume increases.

The size of the bubbles composing the foam: the grade attributed increases as the bubbles become larger.

The density: consistency, staying power of the foam: the grade attributed increases as the density increases.

The softness of the foam: the grade attributed increases as the foam becomes softer.

Stage 5: evaluation during rinsing

The rinsing: the grade attributed decreases as the presence of a slippery film which is difficult to remove increases, which means that the grade increases as the product becomes easier to remove by rinsing without leaving a film.

Turbidity: it is measured as indicated above with a model 2100P turbidimeter from Hach Company.

The sensory results for each of the criteria and the turbidity are as follows:

| Sensory Criteria | Comparative Ex. 1 | Comparative Ex. 2 | Comparative Ex. 3 | Ex. 1 of the invention | Ex. 2 of the invention | Ex. 3 of the invention | Comparative Ex. 4 |
|---|---|---|---|---|---|---|---|
| Foam volume | 4.6 | 7.5 | 6.5 | 5.1 | 5.2 | 5.4 | 5.7 |
| Size of the bubbles | 3.25 | 7.4 | 4.75 | 3.5 | 4.5 | 3.5 | 5.9 |
| Density of the foam | 5.25 | 7.25 | 7.1 | 8.4 | 7 | 7.5 | 6.1 |
| Softness of the foam | 6.5 | 4 | 6.6 | 8.75 | 8.6 | 7.9 | 7.4 |
| Rinsing | 8.6 | 10 | 9 | 8.6 | 8.6 | 8 | 8.6 |
| Turbidity (NTU) | 22 | 15 | 52 | 26.5 | 14.3 | 12 | >1,000 |

It is clear from the above table that Comparative Example 1, which comprises only a phosphate surfactant, gives a foam volume and a density which are insufficient, and moderate softness, that Comparative Example 2, which comprises only an APG, gives an excessively high bubble size (foam which is not fine) and an unsatisfactory softness, that Comparative Example 3, which comprises only the combination of phosphate and APG, gives a softness which is not very high, and that Comparative Example 4, which comprises a surfactant having an insufficient foam height H, gives an excessively high bubble size (thus a foam which is not very fine) and is an opaque gel which, in addition, is unstable over time.

On the other hand, the combination according to the invention makes it possible to simultaneously obtain a transparent gel which gives a fine, dense and also very soft foam while retaining a good foam volume and good rinsing.

The disclosure of French priority Application Number 0009111 filed Jul. 12, 2000 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein

What is claimed as new and is intended to be secured by Letters Patent is:

1. A cleansing composition, comprising:
at least one phosphate surfactant component comprising at least one monoalkyl phosphate surfactant, at least one foaming non-ionic surfactant, and at least one cationic polymer devoid of saccharide groups in an aqueous medium, wherein the composition has the appearance of a transparent gel and wherein the composition does not contain amphoteric surfactant, wherein
   (1) the said at least one phosphate surfactant component is selected from the group consisting of monolauryl phosphate, the potassium salt of dodecyl phosphate, the octyl monoester and octyl diester of phosphoric acid, the ethoxylated (7 mol. Of EO) 2-butyloctanol monoester and the oxylated (7 mol. Of EO) 2-butyloctanol diester of phosphoric acid, the potassium or triethanolamine salts of monoalkyl (C12–C13) phosphate, or potassium lauryl phosphate;
   (2) the said at least one foaming nonionic surfactant is selected from the group consisting of alkylpolyglucosides and polyglycerolated fatty alcohols, and
   (3) the said at least one cationic polymer selected from the group consisting of polyquaternium-5, polyquaternium-47, polyquaternium-7, polyquaternium-39, polyquaternium-28 and polyquaternium-44.

2. The composition according to claim 1, which has a turbidity ranging from 2 to 500 NTU.

3. The composition according to claim 1, wherein the amount of the phosphate surfactant(s) ranges from 1% to 50% by weight of active material based on the total weight of the composition.

4. The composition according to claim 3, wherein said amount of the phosphate surfactant(s) ranges from 1.5% to 20% by weight.

5. The composition according to claim 1, wherein the foaming nonionic surfactant gives a foam height H≧3 cm.

6. The composition according to claim 5, wherein the foaming nonionic surfactant gives a foam height H≧5 cm.

7. The composition according to claim 1, wherein the amount of nonionic surfactant(s) ranges from 1% to 50% by weight of active material based on the total weight of the composition.

8. The composition according to claim 7, wherein the amount of nonionic surfactant(s) ranges from 1.5% to 20% by weight of active material based on the total weight of the composition.

9. The composition according to claim 1, wherein the amount of cationic polymer(s) ranges from 0.01% to 5% by weight of active material with respect to the total weight of the composition.

10. The composition according to claim 9, wherein the amount of cationic polymer(s) ranges from 0.05% to 2% by weight of active material with respect to the total weight of the composition.

11. The composition according to claim 1, wherein the composition is an aqueous composition which in addition to water comprises at least one component selected from the group consisting of lower alcohols, polyols, sugars and their mixtures.

12. The composition according to claim 1, which further comprises at least one thickening agent.

13. A method for cleansing and/or removing make-up from the skin, scalp and/or hair, comprising:
applying the cleansing composition of claim 1 to the skin, scalp or hair; and then rinsing the skin, scalp or hair to remove the cleansing composition.

14. A method for scrubbing and/or exfoliating the skin or scalp, comprising:
applying the cleansing composition of claim 1 to the skin or scalp; and then rinsing the skin or scalp to remove the cleansing composition.

15. A method for cleansing the skin or scalp of grime, comprising:
applying the cleansing composition of claim 1 to the skin or scalp; and then rinsing the skin or scalp to remove the grime and cleansing composition.

16. A method for cleansing the skin, scalp or hair of grease, comprising:
applying the cleansing composition of claim 1 to the skin, scalp or hair; and then rinsing the skin, scalp or hair to remove the grease and cleansing composition.

* * * * *

UNITED STATES PATENT AND TRADEMARK OFFICE
CERTIFICATE OF CORRECTION

PATENT NO. : 7,186,674 B2 Page 1 of 1
APPLICATION NO. : 09/901907
DATED : March 6, 2007
INVENTOR(S) : Veronique Guillou et al.

It is certified that error appears in the above-identified patent and that said Letters Patent is hereby corrected as shown below:

Column 11, line 27, claim 1, after "one" insert --monoalkyl-- and after "surfactant" delete "component";

line 30, delete "and octyl diester";

line 31, change "Of" to --of--;

line 32, change "Of" to --of--;

line 34, change "C12-C13" to --$C_{12}$-$C_{13}$--; and line 35, change "or" to --and--.

Signed and Sealed this

Thirty-first Day of July, 2007

JON W. DUDAS
*Director of the United States Patent and Trademark Office*